United States Patent [19]

Reischl

[11] Patent Number: 4,855,052

[45] Date of Patent: Aug. 8, 1989

[54] FOAM-CONTAINING POLYURETHANE (UREA) COMPOSITIONS AND PROCESS FOR THE PREPARATION THEREOF

[75] Inventor: Arthur Reischl, Leverkusen, Fed. Rep. of Germany

[73] Assignee: Bayer Aktiengesellschaft, Bayerwerk, Fed. Rep. of Germany

[21] Appl. No.: 231,742

[22] Filed: Aug. 12, 1988

Related U.S. Application Data

[60] Division of Ser. No. 141,735, Jan. 11, 1988, Pat. No. 4,801,621, which is a division of Ser. No. 926,770, Nov. 4, 1986, Pat. No. 4,734,439, which is a continuation of Ser. No. 672,439, Nov. 16, 1984, abandoned.

[30] Foreign Application Priority Data

Jan. 26, 1984 [DE] Fed. Rep. of Germany ....... 3402696

[51] Int. Cl.$^4$ .............................................. B01D 29/08
[52] U.S. Cl. ...................................... 210/632; 210/679
[58] Field of Search ................................ 210/632, 679

[56] References Cited

U.S. PATENT DOCUMENTS

| | | | |
|---|---|---|---|
| 2,955,056 | 10/1960 | Knox | 117/98 |
| 3,867,492 | 2/1975 | Drostholm | 264/46.6 |
| 4,082,703 | 4/1978 | Duffy et al. | 260/2.5 |
| 4,229,398 | 10/1980 | Harvey | 264/113 |
| 4,254,177 | 3/1981 | Fulmer | 428/256 |
| 4,393,166 | 7/1983 | Reischl et al. | 525/27 |
| 4,404,296 | 9/1983 | Schäpel | 523/105 |
| 4,419,261 | 12/1983 | Takahashi | 252/182 |
| 4,454,259 | 6/1984 | Reischl et al. | 523/129 |
| 4,734,439 | 3/1988 | Reischl | 521/83 |
| 4,801,621 | 1/1989 | Reischl | 521/83 |

FOREIGN PATENT DOCUMENTS

| | | |
|---|---|---|
| 0026920 | 10/1980 | European Pat. Off. . |
| 2347299 | 4/1975 | Fed. Rep. of Germany . |
| 2929872 | 3/1981 | Fed. Rep. of Germany . |
| 3120121 | 12/1982 | Fed. Rep. of Germany . |
| 3151925 | 7/1983 | Fed. Rep. of Germany . |
| 1341717 | 7/1963 | France . |
| 1574789 | 7/1969 | France . |
| 1574798 | 7/1969 | France . |
| 50-103571 | 5/1975 | Japan . |
| 57-028180 | 3/1982 | Japan . |
| 1230573 | 5/1971 | United Kingdom . |
| 1307468 | 2/1973 | United Kingdom . |
| 1337413 | 11/1973 | United Kingdom . |
| 1478000 | 6/1977 | United Kingdom . |
| 1540076 | 2/1979 | United Kingdom . |
| 2096653 | 10/1982 | United Kingdom . |

OTHER PUBLICATIONS

Tanaka et al., Entrapment of Microbial Cells and Organellps with Hydrophilic Urethane Prepolymers, *European Journal of Applied Microbiology and Biotechnology*, 7, (1979), pp. 351–354.

*Primary Examiner*—Morton Foelak
*Attorney, Agent, or Firm*—Gene Harsh; Joseph C. Gil

[57] ABSTRACT

This invention relates to polyurethane(urea) compositions which contain foam and which are preferably cationically modified, contain non-abrasively bonded fillers and have a very high water absorbability (WAF).

Production is effected by reacting isocyanate-terminated prepolymers with a quantity of water far exceeding the stoichiometric quantity in the presence of foams in particle or film form. The reaction mixture may also contain lignite powder and/or peat, other inorganic and organic fillers and/or biomasses (living cells, living bacteria, enzymes).

The polyurethane(urea) compositions contain up to 95% by weight of foam particles and may contain further fillers (preferably lignite and/or peat). The compositions are swollen and have a high water content during production. Their water absorbability (WAF) when suspended in water is 33 to 97% by weight of water. They can be used as carriers in microbic synthesis processes for the production of complicated organic compounds (when they have incorporated biomasses) as special carriers for the growth of plants, as filter agents or as adsorbents for non water-soluble liquids [for example, crude oil or petrol].

2 Claims, No Drawings

FOAM-CONTAINING POLYURETHANE (UREA) COMPOSITIONS AND PROCESS FOR THE PREPARATION THEREOF

This application is a division of application Ser. No. 141,735, filed 1/11/88, now U.S. Pat. No. 4,801,621, which is a division of Ser. No. 926,770, filed 11/4/86, now U.S. Pat. No. 4,734,439, which is a continuation of Ser. No. 672,439, filed 11/16/84, now abandoned.

BACKGROUND OF THE INVENTION

A number of processes for the impregnation of foams and foam particles have already been described. In such processes, the foams are impregnated with a reactive component (for example with polyisocyanates) and are subsequently reacted with other reactants, (for example polyols, polyamines or vapors of diamines). Typical of such processes are those described in German Offenlegungsschriften Nos. 3,039,146 and 2,131,206, Japanese Pat. No. 50-103 571, French Pat. Nos. 1,587,855 and 1,574,789, and U.S. Pat. No. 2,955,056.

Foams can also be exposed to a liquid having a swelling action. Polyurethane reaction components can then be reacted in the swollen mixture, permitting solidification and rigidification of the foam and optionally allowing inlays to be placed in the swollen foam matrix. Typical of such processes are those described in French Pat. Nos. 1,341,717, 1,587,855, 1,574,798 and German Auslegeschrift No. 1,911,645. Such matrix foams exhibit typical foam properties, although they are somewhat different in hardness, elasticity or chemical and mechanical properties.

A number of other patents describes the adhesion or the pressing of foam particles (preferably polyurethane flexible foam waste) using polyisocyanates, isocyanate-terminated prepolymers and, polyols, polyamines, water or other reactants, optionally with the addition of cork, fibers, cellulose dust, flame-proofing agents, pigments, powdered metals or carbon black, to form novel composite materials. These composite materials are used, for example, as insulating and damping plates, linings, mattresses or molded articles. Suitable processes are described, for example, in British Pat. Nos. 1,337,413 and 1,540,076; U.S. Pat. No. 4,254,177; Japanese Pat. No. 57/028 180 and German Offenlegungsschriften Nos. 2,940,260, 3,213,610, 2,908,161 and 3,120,121.

To date, only the production of block foam from polyurethane foam particles, 10 to 20% by weight of isocyanate compounds, up to approximately 10% by weight of other fillers and small quantities of water have achieved any commercial significance. In this case, the filler consists mainly of color pigments in order to impart a uniform coloring to the composite foam which can consist of foam pieces of differing colors. The water used during the production of the composite foam reacts with the polyisocyanate to form polyurea groups with evolution of carbon dioxide. The quantity of water is selected in such a way that it corresponds approximately to the stoichiometric requirement of the isocyanates, but at most is present in only a relatively small excess since the removal of moisture from the 40 to 60 cm thick composite blocks would cause problems.

The cuttings or scrap produced in industrial quantities when cutting flexible block foam to shape, are preferably used as raw material for the composite foams. The composites, which have a relatively high bulk density, are used as mattresses or elastic carpet underlays. Cuttings (or scrap) are available as scrap polyurethane foam at low cost and in such large quantities that only a proportion thereof can be used for this purpose. The problem of finding an ecologically reasonable and economically advantageous use for the excessive industrial quantities of polyurethane foam scrap has existed for a long time. Elimination of the scrap by burning or dumping is extremely difficult industrially due to the extremely great volume of the scrap.

Water-swollen polyurethane(urea) gels which are either homogeneous or expanded by $CO_2$ generation are also known and described in German Offenlegungsschriften Nos. 2,347,299 and 2,521,265. Such gels are described as containing up to 50% by volume of fillers such as silicates, silica, aluminum oxides, tin oxide, antimony trioxide, titanium dioxide, graphite and graphited coal, retort coal, carbon black, powdered cement, color pigments, fibers and cellulose powder in addition to surfactants or nutrients. The use of foam particles is not described. In this case, the water absorbability of the gels is due to the use of hydrophilic polyurethanes containing 40% or more by weight of oxyethylene sequences.

Water-swollen polyurethane gels, which can contain from 20 to 80% by weight of abrasives such as aluminum oxide, cerium oxide, tungsten dioxide, boron carbide, silicon carbide, carborundum, asbestos dust or diamond dust; graphite; microglass beads; short fibers with an inorganic or organic base, fungicides, dyes or color pigments are also known and have already been described in German Offenlegungsschrift No. 3,151,925. Solid fillers of this type, however, are not water absorbing and cannot display high-water absorbability.

German Offenlegungsschrift No. 3,103,499 describes substantially water-free, polyurethane gel masses using polyols as dispersants. The gels can contain active ingredients, dyes, pigments, fibers, inorganic fillers, powdered metal, activated carbon, cellulose powder and silicas. These polyol-containing gels are not desirable since they tend to give up a large proportion of the dispersed polyol.

The embedding of cells capable of growth in polyurethane hydrogels is also known; see, for example, Tanaka et al., European Journal of Applied Microbiology and Biotechnology, 7, (1979) from page 351. A process for the production of hydrophilic gel-like or foamed biocatalysts with a high charge of enzyme-active substance by polymeric inclusion of complete cells, of cell fragments or enzymes, by mixing an aqueous suspension of the enzyme-active substance with hydrophilic polyisocyanates to form a highly enzyme-active hydrophilic polyurethane network in block or bead form is described in German Offenlegungsschrift No. 2,929,872. Further publications pertaining to the prior art are noted on page 7 of the Offenlegungsschrift.

In the polyurethane gels according to the prior art, it is necessary to build up hydrophilic polyurethanes using polyethers with high ethylene oxide contents in order to achieve an adequate water absorbability. Problems of reactivity of the hydrophilic polyether polyols (which usually exhibit high activity) and problems in the mechanical gel strength when using highly hydrophilic polyether polyols often arise. In addition to the high price of polyurethane gel compositions which are made up in this way, such gels possess only a limited water storage capacity.

DESCRIPTION OF THE INVENTION

It has surprisingly been found that foam, preferably polyurethane foam particles, and in particular, flexible scrap polyurethane foam particles can be used for the production of highly filled, abrasion-proof foam-containing polyurethane(urea) compositions. Such compositions have an extremely high water absorbability and are prepared by reacting isocyanate terminated prepolymers, of hydrophilic or hydrophobic character with water in an amount in excess of that required to react with all the isocyanate groups, in the presence of foam in the form of particles or films and preferably in the presence of further fillers, in particular lignite dust and/or peat. During the production of the resultant highly filled abrasion-proof polyurethane(ureas) the water not only acts as chain extender with formation of carbon dioxide and polyurea but, equally importantly, simultaneously acts as dispersant, causing the foam to absorb the isocyanate compounds and any added fillers uniformly both on the external surfaces and on the internal surfaces of the cells of the foam. When foam particles are used they do not adhere to themselves to form a composite foam during the polyaddition reactions. In other words, the isocyanate compounds act as a selective binder only for the foam (and optionally filler) in and on the foams. It is particularly preferable, especially when using further fillers such as lignite or peat or sea sand to use polyurethane reaction components containing cationic groups or cation-forming groups (for example tertiary amino group-containing polyurethane reaction components), or to add cationic polymers to the reaction mixture. This permits excellent wetting of the foam, lignite or peat and inorganic filler particles during the reaction and also enables the soluble fractions of lignite or peat (which are preferably humic acids) to be retained in an excellent manner in the foam-containing polyurethane(urea) composition. The polyurethane(urea) compositions according to the invention in aqueous suspensions do not exhibit bleeding of, for example, humic acids, which is usually the case with lignite-containing or peat-containing substances.

According to the invention, it is possible but not preferred to add biomasses during polyurethane(urea) formation and thus optionally to incorporate living bacteria, functional cells, cell portions or enzymes into the composition.

It was not anticipated that large quantities of foam particles, preferably approximately in an amount corresponding to the weight of the NCO prepolymers or even significantly more, and optionally further fillers could be bonded non-abrasively in this way by means of the isocyanate compounds (NCO pre-polymers). It was additionally surprising that neither the filler nor the foam particles adhere to each other to form agglomerates of filler or a composite foam. In many cases, even the external shape of the foam is substantially maintained but the water-absorbing properties are significantly improved.

The highly-filled foam-modified polyurethane(urea) compositions produced according to the invention exhibit properties which would not be attainable in a single reaction stage (as usual with the production of polyurethane foams) with all the components contained therein. It is particularly notable that, despite relatively high filler contents, the elasticity of the flexible polyurethane foams which are preferably used, are substantially maintained while the dynamic strain capacity is at the same time considerably increased. Depending on the type of additional filler used, it is also possible to drastically increase the bulk density and to further influence the water absorbing properties and surface activity of the products prepared according to the invention. One of the most important properties achieved according to the invention of the new polyurethane(urea) compositions is their extremely high water absorbability and their stability to wear when they are employed as carriers for biologically fermentative synthesis processes, for example the synthesis of penicillin. It was particularly surprising that hydrophobic isocyanate terminated prepolymers together with the foam and preferably together with further fillers (in particular, lignite and peat) also exhibit excellent water absorbability (WAF). If foam particles are used, they have less tendency to agglomerate. These hydrophobic based compositions are therefore preferred in many cases to hydrophilic based compositions.

The invention therefore relates to a process for the production of a foam-containing polyurethane(urea) composition comprising reacting (A) at least one di- and/or polyfunctional isocyanate-terminated prepolymer having an isocyanate group content of from 2 to 12% by weight, preferably 2.5–8% by weight, (B) from 0 to 50% by weight based on the weight of component (A) of a lower molecular weight di- and/or polyisocyanate with the further proviso that the combination of component (A) and (B) has an isocyanate group content of 30% by weight or less, (C) water, with the quantity of water being in excess of that required to react with all the isocyanate groups of components (A) and (B), preferably in a quantity by weight of from at least twice to about 60 times the weight of components (A) and (B), more preferably the amount of water being from 2 to 30 times and most preferably from 5 to 15 times the weight of components (A) and (B), (D) from 0 to 50 equivalent percent based on the total equivalents of isocyanate groups in components (A) and (B), of an organic di- and/or polyamine; in the presence of (E) from 3 to 95 percent by weight of foam in the form of particles or film, preferably polyurethane foam and most preferably flexible polyurethane foam having a bulk density of 10 to 110 kg/m$^3$ and with particle sizes of from about 1 mm to about 30 mm, or a thickness of up to about 40 mm;

(F) from 0 to 90 percent by weight of lignite and/or peat, preferably lignite dust and/or finely divided black peat, preferably in quantities of 1 to 90% by weight, more preferably 20% by weight or more and most preferably from 20 to 70% by weight, (G) from 0 to 90 percent by weight of other inorganic and/or organic fillers, wherein the percents by weight of (E), (F) and (G) are based on the total moisture-free weight of components (A), (B), (D), (E), (F) and (G) and wherein the sum of components (E), (F) and (G) is from 5 to 95% by weight based on the total moisture-free weight of components (A), (B), (D), (E), (F) and (G), said polyurethane(urea) compositions being abrasion proof in an aqueous medium, being capable of swelling markedly, and having with a water-absorbability (WAF-value) of from 33 to 97% by weight, preferably 80 to 97% by weight. The compositions preferably have a content of cationic groups of 10 to 3000, more preferably 30 to 1500 and most preferably 50–750 milliequivalents of cationic or cation-forming group per 1000 g of components (A), (B) and (D).

The prepolymers useful herein are preferably prepared by reacting
(a) organic materials which contain two or more hydrogen atoms which are reactive with isocyanate groups and which have molecular weights of 400 to 10,000, preferably having a total functionality of 2.1 or more (more preferably 2.5 to 6) and preferably being polyhydroxyl compounds and in particular polyfunctional polyether polyols,
(b) 0 to 5, preferably 0 to 2, moles per mole of (a) of organic materials having molecular weights of 32 to 399, preferably 62 to 254, and containing hydrogen atoms which are reactive towards isocyanate groups, preferred are diols and/or polyols;
(c) organic di- and/or polyisocyanates.

It is also possible to utilize types of components (a) and (b) which contain cationic groups or groups capable of forming cationic groups or to add polymers bearing cationic groups or groups capable of forming cationic groups, preferably with quaternary ammonium groups or salt-forming tertiary amino groups to components (a) and (b). Optionally, compounds containing anionic groups in a quantity corresponding to at most the cation equivalent can also be used.

The polyurethane(urea) portion of the composition, i.e. substantially the weight of the isocyanate-terminated prepolymer used, amounts to from 5 to 95% by weight, preferably from 10 to 75% by weight and most preferably from 14 to 65% by weight, based on the total weight of the composition excluding water, i.e., based on the moisture-free weight of components (A), (B), (D), (E) (F) and (G). In the case that foam particles (E) are used as the only fillers, their content may be from 5 to 95 percent per weight. In combination with other fillers component (E) comprises from 3 to 85 more preferred 5 to 85 percent by weight, with the sum of components (E), (F) and (G) being from 5 to 95 percent by weight. More preferably, component (E) is from 5 to 80 percent by weight, and the sum of components (E), (F) and (G) is from 25 to 90 percent by weight. Most preferably, component (E) is from 7 to 70 percent by weight while the sum of components (E), (F) and (G) is from 35 to 86 percent by weight.

In addition to the foam (E), fillers or type (F) and/or (G) can be used in the specified quantities. Fillers (F) i.e., in particular, lignite dust and/or finely divided (black) peat are preferably used in addition to the foam as they are capable of increasing the water absorbability (WAF) in a particularly desirable manner via their inherent water bonding capacity and the structural properties induced by them. If relatively large quantities (20% by weight or more) of lignite and/or peat are used, the amount of foam used can be very low, for example as low as 0.1% by weight. However, due to the significant modification of properties during the use of the compositions according to the invention, at least 5% by weight of foam is employed. This at least 5% is preferably combined with a lignite and/or peat content of at least 5% by weight. When using lignite and/or peat, a cationic modification of the polyurethane matrix (or cationic polymer addition) is effected in each case. When using hydrophilic polyurethanes (with polyols with 30 or more percent of ethylene oxide) the cationic modification of the polyurethane is used. When using hydrophobic polyurethanes (with less than 30%, preferably less than 20%.) both methods of cationic modification (cationic modified polyurethanes or addition of cationic polymers) can be made.

Other fillers (G), for example inorganic or organic fillers such as mineral coal dust, carbon black, activated carbon, fibers, cellulose dust, cork dust, pigments, iron oxides or powdered metals among others, when used, are preferably used in amounts of less than 50 percent by weight of the amount of component (F). These fillers such as, for example, sea sand, serve to control the density so that the polyurethane(urea) compositions do not float in water. Alternatively they serve—in the case of activated carbon or Aerosil—to increase internal surfaces. The addition of metals or metal pigments, in particular iron oxides such as magnetite, can promote the transfer of oxygen in biological conversion processes.

The invention also relates to the foam containing, polyurethane(urea) compositions preferably containing foam particles and more preferably the foam containing polyurethane(urea) compositions additionally containing lignite and/or peat or optionally further fillers, with high water absorbabilty, characterized in particular by a foam content of from 5 to 95% by weight. The compositions preferably have a cationic group content or cationic group forming content of 30 to 1000 milliequivalents, preferably 50 to 750 milliequivalents per 1000 g of water-free and filler-free polyurethane(urea) composition. When using lignite and/or peat, a cationic modification of the polyurethane matrix (or in some cases) cationic polymer addition is preferably made in each case. The composition also have a water-absorbability (WAF) of from 33 to 97% by weight of water, and preferably 80 to 97% by weight. The foam according to the invention and any lignite and/or peat fillers and optionally further fillers are thus bonded in a polyurethane(urea) matrix. The filler-containing polyurethane(urea) compositions usually are in finely divided or lumped form but the form of course is influenced by the form of the foam.

The compositions according to the invention can be used as carriers, which can be readily suspended in water and which can have biomasses incorporated in them. Such carriers can be used in bio-conversion processes for the production of organic compounds. Additionally, they can be used as carriers containing manure or seeds for plant growth with a high water-bonding capacity, as filtration aids for aqueous suspensions or as adsorbents for non water-soluble liquids such as, for example, (crude) oil or fats in water. Further uses are disclosed in the German patent application No. P 3 402 697.

Suitable foams include, for example, expanded polymers or copolymers of ethylene, styrene, acrylonitrile, (methyl)-butadiene and vinyl compounds. These include, for example, inflated polystyrene granules, expanded polyethylene or foam scraps based on said polymers. These foams are less preferred and are optionally used as component of the mixture in addition to the preferred polyurethane foams.

Flexible polyurethane foam scraps in comminuted form, inevitably produced in large quantities, for example as a mixture of differing bulk densities varying between approximately 10 and 110 (or even 140) kg/m$^3$, preferably 12 to 79 kg/m$^3$ and usually amounting on average to between 20 and 25 kg/m$^3$ are particularly preferably used as foam particles. Rigid and semi-rigid foam scraps can be used for particular applications, but they are generally used only as an additive in finely divided lumped form or preferably in powder form as fillers. Coarser rigid and semi-rigid foams are crushable in many applications even if bonded with polyurethane(urea) and are thus not sufficiently durable, and generally not preferred.

It is very advantageous to use the fine, dust-like scrap inevitably produced in very large quantities during the cutting of rigid polyurethane foam blocks. Even very small quantities produce a change in the properties of the products prepared according to the invention which is desired in some cases. Molded foam waste as well as block foam waste can also be used although it was formerly particularly difficult to utilize such waste due to the high content of smooth external skin or crust.

The process according to the invention is not restricted to use of foam scrap particles. It is also possible, although less preferred, to react flexible foams (preferably polyurethane) in the form of continuous or cut film. The thickness of such films is approximately 2 to 40 mm, preferably 3 to 20 mm The cavities in the foams are filled substantially completely or at least partially during formation of the polyurethane(urea) matrix causing the bulk density and the mechanical strength to increase sufficiently to prevent the foam from floating and to render the foam stable to mechanical influences. According to a preferred embodiment of the invention, finely divided peat and, in particular, lignite dust are used in addition to the foams as filler particles, with cationically (including cation forming) modified polyurethane(ureas) being used as matrix. These carriers can also contain as additional filler, in quantities preferably below 10% by weight, inorganic fillers such as Aerosil, sea sand or iron oxides.

The fillers preferably used according to the invention are peat, for example white or black peat, and lignite. Black peat is the preferred peat. The most suitable filler for the invention, however, is lignite (in its ground form as so-called lignite dust, usually having a residual moisture content of 60% by weight or less, preferably 3 to 20% by weight of water). Due to their strong water-bonding properties, peat and lignite are extremely effective compounds for very effectively increasing the "hydrophilia" or water absorbability of polyurethane(urea) carriers, including those based on hydrophobic polyurethane starting components. It has been found that carriers which are exceptional for use according to the invention with a very high water uptake are formed due to the mechanical structure of lignite or of peat and their water-absorbing effect. Lignite dust, for example, with carbon content of approximately 68%, hydrogen content of 5.3%, oxygen content of 25.7% and nitrogen content of 1.0% (based on dry substance) yields excellent results. Only small quantities of polyurethane(urea) matrix, for example from 5 to 20% by weight, are needed for building up abrasion-resistant foam/filler-containing polyurethane(urea) compositions. Peat and lignite are capable of bonding large quantities of water without feeling wet; for example 150% or more of water, based on lignite or peat dry substances. Even lignite dust from native lignite still contains approximately 40 to 60% of water. Very high filler contents (i.e. bonding with only a very small quantity of polyurethane(urea) matrix) can be achieved with lignite or peat in the presence of polyurethane foams. Dried lignite or peat with water contents of approximately 3 to 20% by weight advantageously exhibit good bonding of humic acid. The polyurethane(urea) carriers which can be obtained in this way from combinations of foams and lignite/peat fillers exhibit particularly desirable water-retaining properties and eminent suitability as carriers in bioconversion processes.

In a particularly preferred embodiment, the foam- and filler-containing polyurethane(urea) compositions contain, in addition to at least 5% by weight of foam particles, from 20 to 85% by weight of lignite and/or peat. Contents of between 20 and 70% by weight of lignite and/or peat are particularly preferred. Compositions according to the invention which contain quantities of foam and lignite or peat of from 35 to 80% by weight are particularly desirable. The use of lignite as additive is most desirable.

In addition to the particularly preferred fillers (F) (lignite and/or peat), it is possible to add further conventional fillers, preferably in amounts of less than half of the quantities of lignite/peat fillers.

The fillers (G) include, for example, organic fillers such as activated carbon, powdered charcoal, mineral coal dust, coke dust, cellulose dust and cork powder; finely divided organic distillation residues melting above 100° C. and in particular distillation residues from toluylene diisocyanate distillation which are obtained, for example, by introduction of the distillation residues in water with denaturation and subsequent granulation. These TDI residues can optionally be modified later on by treatment with compounds containing reactive hydrogens such as ammonia, polyols or polyamine compounds. In many cases, they also contain small quantities of NCO groups or reactive modification products of isocyanates. Distillation residues of this type are known and described, for example, in German Offenlegungsschriften Nos. 2,864,814, 2,846,809 and 2,846,815. High-melting distillation residues of amine, phenols, caprolactam and the like are also suitable distillation residues.

The inorganic fillers of type (G) [such as quartz, sea sand, pyrogenic silica (Aerosil), silicates, aluminosilicates, bentonites, aluminum oxide, pumice stone, siliceous sols, water glass and also calcium oxide, calcium carbonate, diatomaceous earth, heavy spar, gypsum, finely divided iron (II-and/or-III-) iron oxides in pigment form or as magnetites] are preferably added only in proportions in addition to the lignite/peat fillers, to regulate the surface activity and the specific gravity of the carriers so that the carriers sink down or are suspended in water but do not rise up. It is also possible to introduce the fillers of type (G) as the sole fillers in addition to the foam (E).

Fibers (for example inorganic fibers) such as glass fibers or natural or synthetic fibers (for example cotton dust) can also be used as fillers.

The particle size of the fillers (E) and (F) is generally between 0.5 and 1000 μm, preferably below 300 μm, and most preferably below 100 μm. Smaller particle sizes are preferred, in particular, for activated carbon and inorganic constituents and in the case of coal dust or charcoal dust. The peat or lignite dust used according to the invention can possibly be contained as natural fibrous contents.

The quantities of the additives (E), (F) and (G) have already been specified. The proportions of these components are calculated as percent by weight, based on the moisture-free content of the filled polyurethane(urea) compositions. The upper limit is generally determined by consistency and the abrasion-resistance of the highly filled polyurethane(urea) compositions.

The components (E), (F) and (G) are introduced during formation of the polyurethane(urea) matrix in varying ways. For example, they can be mixed with one of the starting materials. For example, they can be added to the isocyanate-terminated prepolymer or to the active-hydrogen containing materials used to make the prepolymer and the polyurethane(urea) forming reaction can then be carried out. However, the foams and/or fillers are preferably first wetted or pasted with water or dispersed in water. Then the addition of the isocyanate-terminated prepolymers, surrounds and bonds them. The polyurethane(urea) is built up simultaneously.

(A) NCO-prepolymers

The starting components for the prepolymers are known for use as polyurethane forming starting components. They include the materials described below.

(a) The starting materials for preparing the prepolymers include organic materials having two and/or more hydrogen atoms which are reactive with isocyanate groups and having molecular weights of from 400 to 12,000. Preferred materials are difunctional and/or polyfunctional higher molecular polyols preferably having functionalities of 2.1 or more, and more preferably 2.5 or more (and up to about 5), and most preferably no higher than 3.5. These higher molecular polyhydroxyl compounds have molecular weights of from 400 to 12,000, preferably 800 to 8000. Polyethers are preferred over polyesters, polycarbonates or polylactones since such polyethers are substantially more stable to hydrolysis in long-term behavior than polyhydroxyl compounds containing ester groups.

Polyoxyalkylene ethers containing a greater number, for example more than 20% (or more than 30% and especially more than 40%) by weight but less than 85% by weight of oxyethylene units are suitable for the preparation of hydrophilic polyurethanes. The oxyethylene groups can be incorporated in the polyethers in a terminal, random or preferably a segment-like fashion. The polyoxyalkylene ethers can also contain small quantities of, for example, cycloaliphatic or aromatic groups. These can be produced by using as initiators, cycloaliphatic polyols or aromatic compounds, such as dihydroxy cyclohexanes or hydroquinone bis-hydroxyethylethers or 4,4'-dihydroxy-diphenyl-dimethylmethane. Suitable polyols can also be made up from higher functional alcohols or sugars by alkoxylation thereof.

It is particularly surprising that hydrophobic polyethers can also be used for making up the polyurethane(urea) matrix. Suitable hydrophobic polyethers include polyoxypropylene polyols without or with small quantities (for example 20% by weight or less) of incorporated oxyethylene segments. Carrier systems based on such polyethers exhibit high water absorbability (WAF) and usually even have an improved long term stability and better sedimentation behavior in aqueous bioconversion media when made up using foam particles, lignite and/or peat and thus are preferred embodiments. On the other hand, filled polyurethane(ureas) which merely have a water absorbability corresponding to the foam content can be obtained using either no additional filler or by using such fillers as mineral coal dust, carbon black, or activated carbon.

Polyethers based on propylene oxide adducts are the preferred polyethers. However, polyethers can also be produced based on other alkylene oxides such as, for example, epichlorohydrin, epoxy butanes or mixtures with, for example, propylene oxide.

Polyether amines with terminal amine groups (for example polyethers obtainable by pressure amination of the secondary hydroxyl groups or cyanethylation and subsequent reduction with terminal aliphatic amino groups), or aliphatic and preferably aromatic polyether amiines formed by alkaline hydrolysis of isocyanate terminated prepolymers are suitable starting materials.

The higher molecular compounds (a) can also contain up to 40% by weight of higher molecular weight polyaddition products, for example from hydrazine hydrate and toluylene diisocyanate. Also, useful are so-called polymer polyols, i.e., those that contain up to 40% by weight of copolymers or graft (co) polymers on the basis of acrylonitrile and (meth)acrylic ester.

(b) Also useful in preparing the prepolymers are lower molecular weight, divalent and/or polyvalent compounds with molecular weights of 32 to 399, preferably 62 to 254. Preferred are diols and/or polyols or amino alcohols such as, for example, ethylene glycol; 1,2-propylene glycol; 1,4-butane diol; 2,3-butane diol; neopentyl glycol; 2-methylpropane diol-1,3; hexane diol-1,6; dodecane diol-1,12; the relatively hydrophilic di-, tri- tetra- and higher molecular polyethylene glycols with molecular weights up to 399; di-, tri- and tetra-propylene glycol diols; or di-, tri- and tetra-oxymethylene diols. Bis-hydroxyethyl-amine, bis-2-hydroxypropylamine, amino sugar or 2-amino-propanediol-1,3, can be used as amino alcohols.

The quantity of (b) is from 0 to approximately 5 moles of (b) per mole of (a). Trifunctional polyols (b) can be incorporated to control the total functionality of the NCO prepolymers.

It is particularly preferable to use cationic groups or groups capable of forming cationic groups in the polyurethane when making up the hydrophilic and/or hydrophobic isocyanate-terminated prepolymers. Suitable cationic groups include quaternary ammonium groups, amino groups, sulphonium or phosphonium groups. The use of compounds containing quaternary ammonium groups or tertiary amino groups is preferred, the latter subsequently being converted into the ammonium or salt form. The quantity of cationic groups or cation-forming groups to be incorporated is preferably from 10 to 3000 millieqivalents of cations or cation-forming groups per 100 grams of components (A), (B) and (D). When quaternarized compounds or compounds which have been converted into the salt form are used, the upper limit is generally 2000 milliequivalents per 1000 g, as an excessively high viscosity would otherwise occur during reaction. The preferred range is from 30 to 1500 milliequivalents of cationic or cation-forming groups and 50 to 750 milliequivalents of cationic or cation-forming groups are most preferably incorporated per 1000 grams.

Diols or polyols containing tertiary amino groups are preferably used as cation-forming compounds. Examples include N-methyl-di-(ethanol) amine or -(propanol) amine; N,N-dimethylaminomethylpropane diol-1,3; bis-hydroxyethyl-piperazine; higher functional compounds such as, for example, triethanolamine; or higher molecular compounds such as, for example, polyoxyalkylene ethers which are started on tertiary amine polyols.

However, hydroxy-functional quaternarized compounds such as, for example, tetrahydroxy alkyl ammonium chlorides or ammonium methyl sulphonates can also be used. Sometimes it is sufficient to use compounds which provide terminal tertiary amine groups into the compounds, for example, N,N-dimethylaminoethanol.

When using these cationically modified polyurethanes (or other cationically modified high polymers), the otherwise water-soluble components of lignite or peat, namely humic acids and similar acidic soluble compounds are surprisingly fixed in a quantitative manner. Therefore, a colorless, completely clear aqueous phase is also obtained when using large quantities of peat and/or lignite. In the past, the use of peat or lignite in aqueous systems was accompanied by the serious disadvantage that the water was rendered brown due to the liberation of considerble amounts of a large number of constituents which were directly soluble or passed into a colloidal solution in water at pH 5 to 9 (for example humic acids or the precursors thereof). Of course, the cationically modified polyurethanes may contain other fillers, such as, for example, sea-sand, instead of or in addition to the peat and/or lignite.

The best method for the production of cationic or cation-forming polyurethane(urea) compositions is by using isocyanate prepolymers which have cationic groups incorporated in them or possess a group capable of forming cations such as nitrogen bonded in the tertiary manner. Conventional acids can be added for salt formation, for example hydrochloric acid, phosphoric acid or sulphuric acid. However, the formation of salt with humic acids is sometimes sufficient.

Instead of incorporated or incorporable cationic components (which is preferred), cationic polymers of a different type, for example aqueous polyurethane or polyacrylate or polyamide dispersions, can be used or added to the reaction mixture. Such polymers can, for example, be used to form an aqueous suspension with the foam plus optionally lignite or peat fillers. Although less preferred such polymers can be used without addition of fillers. If cationic dispersions are added, complete absorption in the highly filled polyurethane(urea) compositions is usually possible only in relatively small quantities, as a proportion thereof will be washed out in the water if excessive quantities are used. It is possible but less preferred, to subsequently add aqueous, cationic dispersions to the non-ionic highly filled polyurethane(urea) carrier material. In this less strongly fixed form, however, the polymer can often act as a flocculant for substances in bioconversion processes. On the other hand, the addition of these cationic polymer additives by addition prior to the isocyanate reaction in an aqueous phase [for example before the isocyanate-terminated prepolymer reacts with water to form the polyurethane(urea)], is more advantageous.

In addition to the cation groups up to (and preferably below) the cation equivalents present of anion groups (for example sulphonate groups) can be present in the polymer or as (polymeric) additives, forming ampholyte systems. An excess of anions over the cation groups should be avoided when using lignite or peat.

The cation groups in the highly filled polyurethane(urea) compositions have a desirable influence not only on the binding of any lignite or peat used, but also on the abrasion-resistance of any additional fillers used. Moreover, the ion charges ensure a finely-dispersed distribution (or even solution) of the isocyanate compounds in the quantities of water used (a type of emulsifier effect), so that undesirable coagulation of the polyurethanes does not occur. Rather the foam and filler particles are surrounded very uniformly by the polyurethane(urea) being formed.

It has also surprisingly been found that inorganic fillers such as quartz, sea sand and pumice stone powder are bonded in a considerably stronger and abrasion-resistant manner by the cationic prepolymers and that no sedimentation of the inorganic fillers occurs during polyurethane(urea) formation. These inorganic fillers are usually added to control the specific gravity of the product in order to prevent the products from floating during biological conversion processes in aqueous solutions. Extremely finely divided inorganic fillers (0.1 to 10 $\mu$m) additionally increases the specific surface area of the carrier compositions. Iron oxides are capable of having a desirable influence on the transfer of oxygen. The inorganic fillers are generally used only in modifying quantities in addition to the other fillers, preferably in addition to lignite and/or peat.

(c) Also necessary in the production of the prepolymers are organic di- and/or polyisocyanates. Preferred isocyanates include difunctional and polyfunctional polyisocyanates, such as, for example, hexane diisocyanate; dicyclohexylmethane diisocyanate; isophorone diisocyanate and the like. Preferred are aromatic di- and polyisocyanates such as toluylene diisocyanate and the isomer mixtures thereof; diphenylmethane-4,4'- and/or 2,4'- and/or 2,2'-isomers; the higher molecular polyphenyl polymethylene polyisocyanates of the type formed by phosgenation of crude formaldehyde/aniline condensation products (polyamine mixtures), which can be used as undistilled sump products. Polyisocyanates containing sulphone groups can also be used.

However, substantially any di- and/or polyisocyanates can be used. Suitable isocyanates are listed in detail, for example, in German Offenlegungsschrift No. 2,832,253. Suitable examples of (a), (b), and (c) are also specified in that Offenlegungsschrift.

The reactive components are reacted with excess quantities of diisocyanates and/or polyisocyanates to form NCO-prepolymers (A) having isocyanate group contents of from 2 to 12% by weight, preferably 2.5 to 8% by weight, and most preferably 2.5 to 6% by weight in the conventional manner, such as, for example, heating of the components at 50° to 100° C. until the prepolymers are formed.

The total functionality of the icosyanate-terminated prepolymers (A) should preferably be at least 2.1, preferably at least 2.5. In other words, it is preferred that at least one of the components should be higher than difunctional.

(B) The NCO prepolymers (A) can be mixed with further quantities of lower molecular di- and/or polyisocyanates (B) in quantities up to 50% by weight of (A) until mixtures of (A)+(B) are formed with isocyanate group contents of 30% by weight or less and preferably 20% by weight or less. Any of the various isocyanates noted above can also be used as component (B). Additionally component (B) can represent the excess of isocyanate used to make the prepolymer itself.

(C) The reaction of the isocyanate-terminated prepolymers (A) or the mixture of (A) and (B) takes place with quantities of water in excess of that required to react with all the isocyanate-groups and preferably in an amount far exceeding the stoichiometric quantity.

The quantity of water used is preferably used to make a paste or dispersion from the foams and any fillers used. The prepolymers are then mixed in. Such prepolymers may first be dispersed in proportional quantities of water. The prepolymers generally thoroughly wet and surround the foam and fillers and then cure relatively slowly with water (more rapidly with addition of diamines or polyamines) to form the polyurethane(urea) matrix. The water reaction can be reduced to a few minutes by increasing the reaction temperature.

Any type of substance conventional in polyurethane chemistry can be used as further additives and/or auxiliaries. Such materials, include, for example, stabilizers, UV-absorbers, dispersants, emulsifiers, silicone derivatives, dyes and pigments. The conventional polyurethane catalysts (such as tertiary amines, metal catalysts or tin catalysts) can be used as catalysts, but this is not absolutely essential in many cases.

It is also possible to include in the reaction mixture (D) organic di- and/or polyamines. Such amines are used in an amount ranging from 0 to 50 equivalent percent based on total isocyanate equivalents in components (A) and (B). When such amines are used, very rapid partial solidification takes place. Examples are ethylenediamine, diethylenetriamine, isophorone diamine, 3,3'.dimethyl-dicyclohexyl-4,4'-diamine, 4,4'-diaminodiphenylmethane, diethyl toluene diamines or aromatic diamines which are alkoxylated with ethylene oxide and/or propylene oxide in quantities of from 0.5 to 2.5 moles alkylene oxide per mol diamine.

The polyurethane(urea) compositions of the present invention exist as somewhat gel-like, swollen (and in some cases foamed) forms which feel moist, when using markedly hydrophilic isocyanate-terminated prepolymers. Compositions produced according to the invention using hydrophobic isocyanate-terminated prepolymers, on the other hand, have a dry feel and thus differ considerably from the gel-like products. The hydrophobic-based products exhibit good abrasion-resistance and surprisingly high water absorbability (WAF). Unlike gels, they can be produced directly in a small-lumped, directly useable form. Therefore they are preferred. In some cases, it is very advantageous to use a mixture of hydrophilic and hydrophobic prepolymers, particularly with regard to the direct formation of lumps. The products of the invention can also be produced by processes and from starting components of the type described, for example, in DE-OS 2,347,299; DE-PS 2,521,277, DE-PS 2,521,265, DE-OS 3,103,500, DE-OS 3,103,564 and DE-OS 3,151,925 (where DE-OS represents a German Offenlegungsschrift and DE-PS represents a German patent).

A preferred method of producing the polyurethane(urea) compositions is by using NCO prepolymers (A), which are produced from excess quantities of polyisocyanate and hydrophobic and/or hydrophilic polyhydroxyl or polyamine compounds (preferably polyether polyols which may contain less than 30% oxyethylene groups) with the optional use of chain extenders and compounds containing cationic groups or groups forming cationic groups. The reaction to form polyurethane(urea) occurs due to the reaction of the isocyanate groups with the excess quantities of water and with any amine groups present (i.e., component (D)). The suspension or wetting of the foams and optionally fillers preferably takes place first. The NCO prepolymer is added thereafter.

In suitable, continuously operating mixer units such as a double blade screw trough, all components can be added substantially simultaneously or only a few seconds after each other and can be mixed thoroughly causing the isocyanate reactions to begin immediately. The reaction rate can be influenced in known manner by means of catalysts and/or by using elevated temperatures. Temperatures between 10° and 90° C., preferably 20° to 70° C. are selected to initiate the isocyanate reaction. In many cases, normal room temperatures are suitable. The reaction temperature can, if desired, be raised to about 90° C. once all the components are mixed.

As already mentioned, water is required not only as reaction component for the polyisocyanate compounds but also as dispersant, in relatively large excess quantities, regardless or whether hydrophilic or hydrophobic isocyanate compounds are used.

The resultant product has a high water absorbability, a high water retention capacity, good abrasion and insolubility in aqueous systems, and a tendency to sink readily or at least an ability to be suspended in the aqueous phase (i.e. a non-floating characteristic).

Maximum water absorbability and retention capacity can be achieved by using starting components which are mainly hydrophilic. An excessively hydrophilic polyurethane(urea) matrix, however, is not usually sufficiently stable with regard to long term storage in water and may not be abrasion-resistant in a fluidized bed. Better stability is achieved by using flexible polyurethane foams, finely divided lignite and/or peat particles in a cationic (or cationic forming) hydrophobic polyurethane(urea) matrix.

The high water absorbability of the composition herein can be achieved in various ways. As a general rule, a significant extent of the water absorbability (WAF value) is affected by the foams used and, by any peat and/or lignite which is preferably used additionally.

The quantity of water present during the reaction with the NCO prepolymers and fillers is of great significance. When using relatively small quantities of excess water, for example 20 parts of water to 80 parts of hydrophilic NCO prepolymer plus fillers, a finely powdered or crumbly, insufficiently hydrophilic and therefore unsuitable product with a high rate of washout is formed. Only with a considerably greater quantity of water does the hydrophobic NCO prepolymer bond the foam and fillers to form an abrasion-resistant water-absorbing carrier with the properties required according to the invention. The NCO prepolymer (in particular, with correspondingly high cationic modification) first surrounds the foam and filler particles in a sufficiently wetting manner and then reacts to form the polyurethane(urea), enclosing the foam particles and also the preferred lignite or peat particles firmly in a water-permeable manner.

The proper amount of water for any combination of foam, filler and prepolymer can generally be determined by conducting small scale experiments. Thus, approximately 30 to 300 g samples of the highly filled polyurethane(urea) compositions, which are under consideration (and which have been produced by systematic variations of the type and quantity of isocyanate components, foams and fillers in the presence of variable but ever increasing excess quantities of water) are subjected to a test in water-filled columns (for example with a diameter of 10 to 20 cm), through which air is allowed to flow from below via a frit or a finely perforated die plate. The abrasion, the sinking tendency, the color and the transparency of the aqueous phase can easily be determined within 24 hours. The presence and correct metering of excess quantities of water, as explained, is of great importance in the production of a carrier material for use as bioactivators in biological conversion processes and can be optimized by simple preliminary tests according to the information given.

The shaping of the highly filled polyurethane(ureas) is determined by the requirements of the proposed application. Regular or irregular lumps of granulated material can be obtained either directly or by the conventional cutting or granulation methods thereby forming block, strand or ribbon-shaped products. In some cases, highly filled polyurethane(ureas) to be used according to the invention are suspended in film form or wound in a spiral coil for use in bioreactors. In these cases, textile backings can be used to stabilize particularly large surfaces.

In the cheapest and simplest embodiment, the carriers are used in the form of an irregular granulate in a size of 0.1 to 10 cm, preferably 1 to 3 cm. For this purpose, the substantially or completely reacted highly-filled polyurethane(ureas) (optionally in prefabricated strands, block or strip form) are comminuted to the suitable lump size using conventional choppers or cutting granulators. Any fine grains can be isolated during washing and separated.

If the isocyanate reactions are carried out intermittently in kneaders or in mixing apparatus equipped with, e.g., blades, subsequent comminution is not usually necessary.

The water-swollen carrier compositions according to the invention are generally elastic, abrasion-resistant particles which feel fairly moist and which can be suspended in water and sink slowly in it. In the case of a purely hydrophilic polyurethane(urea) matrix, the compositions are less water-swollen than water-bonding (for example, via the foam structure and optionally hydrophilic fillers).

It could not be anticipated that the polyurethane(urea) compositions highly filled predominantly with light foams and preferably fillers such as lignite or peat could be produced in a sufficiently abrasion-proof manner with a homogeneous, usually lumped structure and have such a desirable influence on bioconversion processes even though fillers of an active nature such as, for example, black peat and lignite are embedded within the polyurethane(urea) matrix.

The compositions of the invention are suitable for many of the conventional bioconversion processes, for example for the production of citric acid from starch, for the hydrolysis of penicillin G using acylases to form 6-amino penicillic acid, for the production of stereospecific biologically active compounds or for the fermentation of sugar-containing waters in the sugar beet industry.

The foam and any optional filler incorporated in the polyurethane(urea) has an advantageous influence on the improved bioconversion process in many respects. Depending on the type of foam and filler and the type of polyurethane(urea) matrix, the mechanical strength and the water absorbing and water retaining properties of the polyurethane(ureas) are improved. The bioactive assimilation capacity of the organic substances to be converted is surprisingly substantially increased. Moreover, the filler or the filler mixture bonded in the polyurethane(urea) composition acts simultaneously as a control for maintaining optimal specific gravities for the compositions which are permeable to water, so that a uniform distribution of the carriers with a slight sinking tendency or the maintenance of a suspended state is possible in the conventional containers. This is of particular importance in most processes and may even be a requirement in some processes.

Flexible polyurethane foam (or scrap) having low bulk densities (e.g. from 20 to 35 kg/m$^3$), is completely changed from its original structure and physical properties and can be used in bioconversion processes after reaction according to the present invention. A sufficient quantity of water may be bound in the cavities of the foam (which may be partially filled). It is thus possible to use flexible foam in combination both with hydrophobic and hydrophilic isocyanate-terminated prepolymers and preferably with additional hydrophilic fillers such as lignite or peat. An advantageous structure on which bacterial growth into the remaining cavities of the modified foam can take place is formed due to the interaction of the hydrophilic fillers (preferably peat or lignite) and the quantities of physically bonded water. Inorganic fillers in very finely divided form can also be used during the production of these highly filled polyurethane(urea) compositions to regulate the specific gravity to prevent floating in aqueous reaction fluids, for example during bioconversion processes.

The degree of water-absorbability is preferably adjusted in such a way that a high water absorption takes place within hours or a few days with marked swelling or that a greater quantity of water is present as disperse phase during the production of the polyurethane(urea) compositions and the carriers are thus already completely swollen.

The "in situ" incorporation of microorganisms into polyurethanes or other plastics, even under very careful and technically complicated conditions, is not possible without substantial loss of bacteria capable of propagation and a marked reduction in bioactivity. The production conditions should be controlled, in particular with respect to the temperature (approximately +10° C.). Nevertheless, this technique is not preferred and is usually not necessary since the growth of biomasses into the polurethane(urea) carrier takes place readily.

The usefulness of the polyurethane(urea) compositions of the invention (preferably containing foams and lignite or peat embedded in cationic modified polyurethane(urea) matrix) lies in their high water absorbing property. They can be used as soil conditioners or special growth agents of a hydrophilic easily rooting type for plants since they can contain plant nutrients, they have very long utilizable water contents and can have manure contents.

Seeds can also be added to the compositions during production and are then caused to germinate and can be utilized, for example, in tray forms, for example as lawns of parsley or can be used in small lumped form for plant layering.

Another important way of using the compositions of the invention is as carriers for bacteria or enzymes in bioconversion processes for the production of complicated organic compounds. The lumped carriers can easily be removed from the reaction or fermentation vapors by filtration. The lumped carriers can also be used as filtration medium for finely divided impurities and can be regenerated, for example, by back washing. The carriers according to the invention are used particularly effectively as adsorbents for (crude) oil or other non-water-soluble organic fluids. A further, important application of the carriers is claimed in the German patent application No. P 3 402 697.5 for sewage treatment.

The invention is further illustrated but is not intended to be limited by the following examples in which all parts and percentages are by weight unless otherwise specified.

EXAMPLES

(A) Production of the Carrier Compositions

(A1) Production of the NCO-Prepolymers

The NCO-prepolymers are produced in a known manner in a mixing apparatus by heating the starting components noted in Table 1 for about 2 to 3 hours at temperatures of from about 70° to 90° C. until the calculated NCO content is obtained.

TABLE 1

Composition and characterization of the NCO-prepolymers (PP)

| Type | Viscosity mPas/25° C. | % NCO | Isocyanate Quantity/type | Polyetherpolyol Quantity/type | NM | DMS | IQU |
|---|---|---|---|---|---|---|---|
| KI-PP-A | 12,500 | 5.1 | 16.6 TDI | 80.4 PHILV | 1.5 | 1.5 | 120 |
| KIO-PP-B | 6,400 | 5.3 | 19.1 TDI | 57.1 PHILV | 2.5 | 2.4 | 200 |
|  |  |  |  | 19.0 PHOBL |  |  |  |
| KI-PP-C | 11,200 | 5.6 | 18.5 TDI | 79.1 PHILV | 2.4 | 2.4 | 200 |
| I-PP-D | 56,000 | 4.9 | 22.4 D44R | 77.6 PHILV | — | — | — |
| KO-PP-E | 9,500 | 5.9 | 20.0 TDI | 41.9 PHOBV | 1.5 | 1.5 | 120 |
|  |  |  |  | 35.0 PHOBL |  |  |  |
| KO-PP-F | 12,200 | 3.2 | 14.1 TDI | 45.9 PHOBV | 0.8 | 0.8 | 60 |
|  |  |  |  | 38.4 PHOBL |  |  |  |
| (K)O-PP-G | 15,600 | 5.7 | 20.6 TDI | 76.3 PHOBV | 3.1 | 3.1 | 260 |
| O-PP-II | 7,800 | 3.3 | 11.9 TDI | 88.1 PHOBV | — | — | — |
| O-PP-I | 18,300 | 3.6 | 7.7 TDI | 80.1 PHOBV | — | — | — |
|  |  |  | 12.2 D44R |  |  |  |  |

Type = Characterization of the NCO-prepolymers (PP) (the last letter, i.e. A through I, is only used for designaton purposes.
K = Cationic
(K) = Cation-forming Lertinry amino-groups
I = Hydrophilic
() = Hydrophobic
(Quantities as parts by weight).

The quantities in Table 1 are given as parts by weight. The materials used were as follows:

Isocyanates used:

| TDI = | toluylene diisocyanate-2,4- and -2,6-isomeric mixture (80:20 wt. ratio) |
| D 44 R = | distillation residue from the production of 4,4'-diphenylmethane diisocyanate containing proportions of higher molecular polyphenyl polymethylene polyisocyanates, NCO content 29.8% by weight. |

Polyetherpolyols:

| PHILV = | hydrophilic, branched polyether from trimethylol propane reacted with 40 parts of propylene oxide and 60 parts of ethylene oxide, OH-number 26. |
| PHOBV = | hydrophobic, branched polyether derived from trimethylol propane reacted with 80 parts of propylene oxide and then 20 parts of ethylene oxide, OH number 28. |
| PHOBL = | hydrophobic, linear polyether from 1,4-butene diol and propylene oxide, OH number 56. |

Compounds with tertiary nitrogen:

| NM = | N—methyl-diethanolamine. |

Quaternization agent:

| DMS = | dimethylsulphate. |
| PPS = | 85% polyphosphoric acid. |

Ionification details:

| IQU = | cation equivalent or tertiary nitrogen equivalent (as cation-forming group) in milliequivalents per 1000 g of NCO prepolymer. |

(A2) Reaction of the NCO-Prepolymer to Form the Polyurethane(urea) Compositions The foam particles and optionally fillers are suspended in the specified quantity of water or the water is stirred into the foams/fillers. The NCO prepolymer is then rapidly and intensively mixed at room temperature. When hydrophilic NCO-prepolymers are used, the reaction mixture solidifies at room temperature after only a few minutes (for example 1 to 3 minutes). When hydrophobic prepolymers are used the mixture hardens after 1 to 2 hours. The reaction time can be reduced to a few minutes by addition of 0.1 to 0.5% by weight of catalysts, based on the quantity of prepolymer, and/or by the use of hot water (about 80° C.). The reaction takes place in a conventional mixing apparatus (in the case of laboratory preparations). Horizontally positioned, conventional mixing devices equipped with bladed mixing tools are preferably used for industrial quantities.

If the cations have not yet been (from tertiary amino groups) formed in the prepolymer (for example by quaternization), the calculated quantity of acids or quaternization agents (preferably phosphoric acid) is added to the aqueous filler suspension to form the amine salt. If lignite or peat is used as filler, the humic acids contained therein are utilized for salt formation, with the formation of polyurethane-humates.

The compositions according to the invention, produced in this way sediment completely in water at various speeds depending on the composition.

(A3) General Instructions for the Continuous Mode of Preparation

A double blade screw trough with a capacity of about 180 liters and a length of about 300 cm which is equipped with a heating jacket for hot water or steam and whose blade shafts rotate in opposing directions is used as apparatus. The product is conveyed from the inlet opening towards the outlet opening, a certain kneading or squeezing of the reaction mixture taking place between the blade shafts. The comminuted polyurethane foam and optionally the fillers and other additives are preferably conveyed separately via metering screws into the screw trough. At the same point, the water is introduced by piston pumps and the NCO prepolymer by gear pumps. It is preferable to mix the cationic NCO prepolymers intensively within a few seconds with about 10 times the amount of water at about 10° to 25° C. in a diffusion mixer or static mixer since the fillers (in particular the pre-dried lignite powder or peat) are then wetted extremely quickly and uniformly with the separately added remaining quantity of water (optionally heated to 90° C.) and the NCO prepolymer in very finely divided form uniformly surround the solids and foams.

In most cases, a residence time in the screw trough of about 1 to 8 minutes is sufficient, but it is preferable to adjust a residence time to about 2 minutes. The material produced (optionally with catalysts and/or at elevated temperature) is discharged through an opening in the container located at the bottom at one end of the trough and is suspended in water or sprayed for complete swelling with water immediately or at a later time.

(A4) Comparison Examples (Not According to Invention)

Reactions of the NCO prepolymers (see Table 1 for their composition) are carried out in excess quantities of water but without using foams or fillers to form polyurethane ureas.

(a) Use of Hydrophilic NCO-Prepolymers

If the NCO prepolymers (KI-PP-A, KIO-PP-B, KI-PP-C or I-PP-D) are stirred at room temperature into 5 to 10 times the quantity by weight of water, an aqueous solution is initially obtained from which there is formed within 1 to 2 minutes a polyurethane foam gel which floats even after weeks of storage in water (i.e., does not settle) and which therefore cannot be used as carrier in bioconversion processes by the fluidized bed technique. Foam-gel formation takes place within 20 seconds at 50° C. and higher, the proportion of closed cells being even higher, further impairing their usefulness.

(b) Use of Hydrophobic, Cationic NCO-Prepolymers

The cationic, hydrophobic NCO-prepolymers such as KO-PP-E and KO-PP-F react considerably more slowly at room temperature in 5 to 10 times the quantity of water and can initially be dispersed finely in water. However, a powder deposit which cannot be used forms within hours in the reaction vessel.

A deposit is formed within 40 seconds at temperatures of 50° C. and higher.

(c) Use of Hydrophobic Non-ionic NCO-Prepolymers

Dispersion of such NCO-prepolymers in large excess quantities of water is not possible as solidification into a fairly sticky mass which gradually solidifies at room temperature.

EXAMPLE 1 (Detailed Example of Production)

Carrier Composition 6.5 parts by weight of a flexible foam granulate WSB-90 and 9.44 parts by weight of a native lignite from the Aachen lignite region (with 11% residual moisture), which has been comminuted to particles below 100 m and thus has the form of lignite powder are stirred into 80 parts by weight of water at 18° C. and stirred in accordance with the process described in Example A2, with 5.0 parts by weight of the cationic NCO-prepolymer KI-PP-A (5.1% by weight NCO (see Table 1)). A carrier material in the form of a water-swollen, elastic solid which has a moist feel and is granulated into pieces below a size of 12 mm is produced. The solid cationic polyurethane(urea) carrier material filled with foam and lignite contains 42.5 g of lignite-dry substance and 32.5 g of foam in 100 g of moisture-free carrier composition. Consequently, the composition contains 75% by weight of foam plus lignite based on the dry mass of the filled polyurethane(urea) composition.

The granulated carrier material obtained is then mixed with excess water for 24 hours (at room temperature), completely swollen and the water over the swollen carrier is decanted off. The value derived from this which indicates the percentage by weight of water in and between the swollen carrier (filler-containing polyurethane urea) is designated herein as water absorbability (WAF).

The solids content of the aqueous suspension of the granulate thus obtained in the form of a now markedly swollen carrier material amounts to 108 g of solids per liter of "suspension" (without overlying water). The solids content in 1 liter of such a suspension (without overlying water) is designated as the dry substance of the suspension (abbreviated to TS-S). TS-S is determined by completely drying the suspension.

The weight of 1 liter of the suspension of the markedly swollen carrier material (without overlying water) is designated as suspension weight (abbreviated to SG).

The value of the so-called suspension factor (F4) is determined from the suspension weight (SG) and the dry substance of the suspension (TS-S) which is contained therein. The value of the suspension factor F4 minus 1 (F4−1) gives the quantity of water (based on dry carrier substance) in the suspension (in the form of swelling water and as water in the cavities in or between the carrier particles).

The value of the suspension factor F4 is determined in practice by first determining the dry substance of the suspension (TS-S). The suspension weight (SG) is then divided by the dry substance (TS-S) contained therein:

$$F4 = \frac{SG}{TS - S}.$$

The water absorbability (WAF) is expressed as a percentage and can be determined from the suspension factor F4 as a characteristic of the carrier compositions to be used according to the invention from the following formula:

$$WAF = \frac{F4 \text{ minus } 1}{F4} \cdot 100 = (\text{in } \%)$$

This water absorbability (WAF), expressed as a percentage, gives an idea of the state of the highly swollen carrier compositions as are used in the swollen state in an aqueous medium. In Example 1, for example, the dry substance of the suspension (without supernatant water) is 108 g of solids. The suspension factor $$F4 = \frac{1004}{108} = 9.3$$

is then calculated since a suspension weight of 1004 g per liter of suspension. 1 part by weight of dry substance of the carrier composition is thus converted with 8.3 times the quantity of water into the described swollen suspension form. In other words, the water absorbability=(8.3 by 9.3) times 100=89.2%.

For further characterization of the carrier compositions the apparent densities (g/l) are determined after different types of treatment under the following conditions:

S1. Apparent density, drained off: The carrier composition is suspended for 24 hours in a large excess quantity of water. A sieve with 2 mm sieve holes is filled to 10 cm high with this swollen composition and allowed to drain for 1 hour. The remaining material is then weighed in a measuring vessel and converted to the apparent weight per liter.

S2. Apparent density, crushed out: The carrier composition drained according to S1 is subjected to a pressure of 3 bars on a 1 mm sieve for 5 minutes and then weighed in a measuring vessel. The apparent density S2 is calculated.

S3. Apparent density, dried: The moist carrier composition crushed out according to S2 is dried for about 1 day at 110° C. under vacuum until the weight is calculated and is then weighed in a measuring vessel. The apparent density S3 is then calculated.

In Example 1 given above, the values determined for S1 to S3 are:

S1 (drained off) 536 g/l
S2 (crushed out) 403 g/l
S3 (dried) 14 g/l

The following factors can also be determined for better comparison:

F1: The volume factor is the quotient of the apparent density, drained off (S1) and the weight of the dry substance of one liter of the suspension (TS-S).

$$F1 = \frac{S1}{TS - S} \cdot \text{In Example 1, } F1 = \frac{536}{108} = 4.96.$$

F2: The crush factor corresponds to the quotient of apparent density, crushed out (S2) and the weight of the dry substance of one liter of the suspension (TS-S).

$$F2 = \frac{S2}{TS - S} \cdot \text{In Example 1, } F2 = \frac{403}{108} = 3.73.$$

F3: The swelling factor is the quotient of the apparent density, drained off (S1) and the weight of the dry composition determined after complete removal of the water from one liter of the drained sample (TS-S1)).

$$F3 = \frac{S1}{TS - S1} \cdot \text{In Example 1, } F3 = \frac{536}{111.6} = 4.8$$

The volume, crush and swelling factors should be at least 2, preferably at least 3, and more preferably at least 4. The upper limits of the specified factors are below about 20 and preferably below 15. Moreover, the three factors of the same sample should differ as little as possible, i.e. by a maximum of 3 times, preferably by only about 2 times.

The results of Example 1 are compiled in Tables 2 and 3.

Characteristic of the foams used as fillers in the Examples.

(a) Flexible foams: Three flexible foams WSB 14 and 90 WSF 61, which are mixtures of differing bulk density (from about 15 to about 110 kg/m$^3$) from the mass production of polyether polyurethane blocks and molded foam were used.

WSB-14: The dry bulk density of the flexible foam consisting predominantly of block foam scrap is approximately 14 g/l. Particle size was from 1 mm to 20 mm. Apparent densities after suspension in water S1: 263 g/l; S2: 101 g/l; S3: 14 g/l; TS-S (content of dry substance in water suspension): 12.5 g/l.

WSF-61: Molded flexible foam scrap with a very high proportion of crust (tough external skin), apparent densities: S1: 365 g/l; S2: 199 g/l; S3: 61 g/l; TS-S: 51.7 g/l.

WSB-90: Fexible block foam scraps: particle size from 1 to 12 mm; apparent densities S1: 365 g/l; S2: 199 g/l; S3: 40 g/l; TS-S 35 g/l of suspension.

(b) Rigid-block-foam-scraps

HSB-65 The apparent densities of the granulate consisting of block rigid foam scraps with particle sizes below 2 mm was: S1: 896 g/l; S2: 457 g/l; S3: 65 g/l.

Comparison tests with unmodified foams

Polyurethane foams which are not bonded with polyurethane(urea) are quite unsuitable in practice for bioconversion processes since the foams float to the top. In a further comparison test in a mixing apparatus, using a flexible foam having a relatively high density (bulk density 36 g/l; weight per unit volume 90 g/l) (comminuted to a size below 12 mm), the majority of the material immediately floated to the top during a short interruption in the stirring action after 3 months storage in water. It was not possible to use a fluidized bed with this foam. Rigid polyurethane foams are also unsuitable as they float to the top, are too brittle and lead to abrasion.

Production of the Carrier Material According to the Invention

The highly filled polyurethane(urea) compositions used in Examples 1 to 21 (excluding Examples 2 and 8) are produced according to Example A2 at about ambient temperature either in an intensive mixer consisting of a cylindrical container which is obliquely fixed to a rotatable plate and is equipped with an eccentrically introduced stirrer, which rotates in the opposite direction to the plate, or horizontally mounted mixers are used which are equipped with blade-like tools.

The comminuted polyurethane foam scrap and the required quantity of water are introduced, and the filler (for example, lignite) is mixed in uniformly. The NCO-prepolymer is subsequently added in a fine stream by means of a gear pump. The catalyst K is optionally added as the last operation (in the form of an aqueous emulsion diluted to 20-fold). Stirring is interrupted after a few minutes, once all components have been mixed in and the carrier material is then spread in a layer approximately 10 cm deep for 10 to 90 minutes until the isocyanate reactions have substantially ended.

The carrier material is washed several times with a large amount of water and can then be used immediately or at a later time.

The compositions of the carriers according to Examples 1 to 21 are reproduced in Table 2; and the properties thereof are set forth in Table 3.

TABLE 2

Composition of the highly filled polyurethane(urea) compositions for Examples 1 to 21 (intermittent production process according to Example (A) 2, except in Examples 2 and 8, which were produced continuously according to Example (A)3.)

| Patent Examples | Fillers (scrap) Quantity | foam Type | Sieve size (μm) | Other fillers Quantity | Type | Sieve size (μm) | NCO-Prepolymer Quantity | Type | % NCO content | Water Quantity | Water Temp | Addition Quant | Addition Type | Dry Substance (g/l) Suspension (TS(S)) | Apparent densities Dripped Off S1 | Crushed Off S2 | Dried S3 |
|---|---|---|---|---|---|---|---|---|---|---|---|---|---|---|---|---|---|
| 1 | 6.5 | WSB-90 | 12 | 8.5 | BKS | 100 | 5 | KIPP A | 5.1 | 80 | 18° C. | — | — | 108 | 536 | 403 | 144 |
| 2 | 5.0 | WSB-90 | 12 | 20.0 | TDIR | 100 | 5 | KIOP B | 5.3 | 70 | 30° C. | — | — | 143 | 636 | 500 | 246 |
| 3 | 10.0 | WSB-14 | 12 | 10.0 | BKK | 100 | 7.5 | KOPP F | 3.2 | 77.5 | 85° C. | K 1 | — | 56 | 533 | 175 | 60 |
| 4 | 7.5 | WSB-14 | 20 | 10.0 | BKS | 100 | 3.0 | KIPP A | 5.1 | 78.5 | 18° C. | K | Fe-1 | 62 | 593 | 283 | 69 |
| 5 | 7.5 | WSB-14 | 20 | 10.0 | BKS | 100 | 5.0 / 2.5 | OPP I / KOPP E | 3.6 / 5.9 | 75 | 35° C. | — | — | 56 | 366 | 213 | 58 |
| 6 | 7.5 | WSB-14 | 12 | 10.0 | SK | 90 | 7.5 | OPP I | 3.6 | 75 | 35° C. | K | — | 59 | 368 | 164 | 60 |
| 7 | 7.5 | WSB-14 | 12 | 10.0 | BKS | 100 | 7.5 | OPP I | 3.6 | 75 | 35° C. | K | KPUD | 54 | 382 | 180 | 56 |
| 7a* | 7.5 | WSB-14 | 12 | 10.0 | BKS | 100 | 7.5 | OPP I | 3.6 | 75 | 35° C. | 1 | KPA | 56 | 354 | 187 | 58 |
| 8 | 10.0 | WSB-14 | 12 | 10.0 | T | 100 | 5.0 | KOPP E | 5.9 | 75 | 60° C. | K | — | 68 | 460 | 184 | 55 |
| 9 | 5 | WSB-14 | 20 | 6 | BKK / TDIR | 100 | 3.5 / 1.5 | KIPP A / IPP D | 5.1 / 4.9 | 79 | — | — | — | 79 | 448 | 306 | 87 |
| 10 | 7.5 | WSB-14 | 12 | 5 | BK | 100 | 3.5 / 3.5 | KOPP E / KOPP F | 5.9 / 3.2 | 79 | — | K | — | 44 | 528 | 200 | 66 |
| 11 | 5 | WSB-14 | 20 | 10 | BK | 90 | 6 / 3.5 | KOPP E / KIOPP B | 5.9 / 5.3 | 79 | — | K | — | 85 | 470 | 295 | 84 |
| 12 | 20 | WSF-61 | 12 | 10 | BK | 100 | 3.5 / 1.5 | KIOPP B / OPP H | 5.3 / 3.3 | 65 | — | — | — | 110 | 581 | 328 | 100 |
| 13 | 7 | WSB-14 | 12 | 7 | AK | 30 | 5 | KIPP A | 5.1 | 80 | — | — | — | 60 | 471 | 201 | 66 |
| 14 | 7.5 | WSB-90 | 12 | — | — | — | 5 | KIPP A | 5.1 | 85 | — | — | — | 60 | 579 | 479 | 131 |
| 15 | 7.5 | WSB-14 | 12 | — | — | — | 2.5 / 3.0 | IPP D / KOPP F | 4.9 / 3.2 | 84.5 | — | 5 | Fe-1 | 40 | 514 | 124 | 31 |
| 16 | 3.5 | HSB-65 | 12 | 25 | BK | 100 | 20 | KIPP A | 5.1 | 50 | — | 1.5 | SIG | 112 | 581 | 328 | 151 |
| 17 | 10 | WSB-14 | 12 | 10 | BK | 100 | 4 | KIPP A | 5.1 | 72 | — | — | — | 58 | 610 | 428 | 86 |
| 18 | 7 | WSB-14 | 12 | 10 | BK | 100 | 4 / 5 | IPP D / KIPP A | 4.9 / 5.1 | 76 | — | 2 | Fe-2 | 74 | 631 | 346 | 90 |
| 19 | 10 | WSB-14 | 12 | 5 | BK | 100 | 5 | KIPP C | 5.6 | 78 | — | 2 | SIW | 56.8 | 632 | 234 | 67 |
| 20 | 10 | WSB-14 | 6 | 10 | BK | 100 | 4 | KOPP E | 5.9 | 76 | — | K | — | 47 | 506 | 262 | 58 |
| 21 | 4.5 | WSB-14 | 12 | 11 | SK | 90 | 3.5 | KIPP A | 5.1 | 81 | — | — | — | 54 | 562 | 278 | 64 |

*Comparison Experiment.
(Quantities in parts by weight, based on dry substance).
Quantities given in parts by weight, each based on solids.
K = 0.5% by weight of dibutyl tin dilaurate, (in parts by weight of NCO prepolymer
BK = lignite - native (in parts by weight of dry substance)
BKK = lignite coke
T = black peat (residual moisture 8.4% by weight of water)
AK = activated carbon
SK = mineral coal dust (anthracite dust)
TDIR = TDI sump residue stirred out in water, ground below 200 μm.
Fe-1 = Ferromagnetic iron oxide ($Fe_3O_4$), particle size about 1 μm
Fe-2 = Iron oxide pigment ($Fe_2O_3$), particle size about 1 μm
SIG = silica sol, 30% in water, specific surface area 200 $m^2/g$
SIW = water glass, 10% solution with 5% by weight of phosphoric acid, added after start of gelation
KPUD = aqueous, cationic polyurethane dispersion
KPA = aqueous, cationic polyamide dispersion (Praestol 185 K, Fa. Stockhausen, Germany)
BKS = lignite-dust

TABLE 3

Volume, crush and swelling factors of the highly filled polyurethane(urea) carrier compositions (Examples 1 to 21)

| Example | F 1 Volume Factor | F 2 Crush Factor | F 3 Swelling Factor | F 4 Suspension Factor | WAF Water Absorbability % | % FKS Solids content |
|---|---|---|---|---|---|---|
| 1 | 5.0 | 3.7 | 4.8 | 9.3 | 89.2 | 10.8 |
| 2 | 4.4 | 3.5 | 3.1 | 7.4 | 86.1 | 13.9 |
| 3 | 9.5 | 3.1 | 6.1 | 18.2 | 94.5 | 5.5 |
| 4 | 9.6 | 4.6 | 5.7 | 16.3 | 93.8 | 6.2 |
| 5 | 6.3 | 3.7 | 4.7 | 17.4 | 94.3 | 5.7 |
| 6 | 6.2 | 2.8 | 4.3 | 17.1 | 94.2 | 5.8 |
| 7 | 7.1 | 3.3 | 4.9 | 18.7 | 94.7 | 5.3 |
| 8 | 6.7 | 2.7 | 4.2 | 14.2 | 93.1 | 6.9 |
| 9 | 5.7 | 3.9 | 5.9 | 13.2 | 92.4 | 7.6 |
| 10 | 12.0 | 4.5 | 6.5 | 22.9 | 95.6 | 4.4 |
| 11 | 5.5 | 3.5 | 5.1 | 12.0 | 91.7 | 8.3 |
| 12 | 5.3 | 3.1 | 4.5 | 9.2 | 89.1 | 12.9 |
| 13 | 7.3 | 3.1 | 4.8 | 15.7 | 93.6 | 6.4 |
| 14 | 9.7 | 8.2 | 8.4 | 16.9 | 44.1 | 5.9 |
| 15 | 13.0 | 3.1 | 8.3 | 25.2 | 96.1 | 3.9 |
| 16 | 3.6 | 3.4 | 3.1 | 7.0 | 88.9 | 11.1 |
| 17 | 10.5 | 7.4 | 5.6 | 17.4 | 94.3 | 5.7 |
| 18 | 8.5 | 4.7 | 6.3 | 13.7 | 92.7 | 7.3 |
| 19 | 11.1 | 4.1 | 6.5 | 17.7 | 94.4 | 5.6 |
| 20 | 10.7 | 6.1 | 6.1 | 21.3 | 95.3 | 4.7 |
| 21 | 10.4 | 5.1 | 6.1 | 18.7 | 94.7 | 5.3 |
| Average value X = | 8.0 | 4.2 | 5.5 | 15.7 | 93.0 | 7.1 |
| Lower-upper Limit | 3.6–13.0 | 2.7–8.2 | 3.1–4.8 | 7.0–25.2 | 86.1–96.1 | 3.9–13.9 |

The difference in the WAF value (water absorbability) from 100 represents the percentage of solids-content (% FKS) in the suspension (without overlying water).

Re Example 7a* (with cationic polyamide dispersion) This is a comparison with Example 7 in which a cationic polyurethane dispersion has also been added and a comparison with Example 5 in which one third of the NCO prepolymer is replaced by a cationic prepolymer.

The cationic polyamide dispersion used in Example 7a is washed out in a much more pronounced fashion in the aqueous suspension of the carrier material than in Example 7 with a cationic polyurethane dispersion and is therefore less suitable. The carrier from Example 5 is very good. Brown discoloration (humic acid solution) of the aqueous phase which makes the carrier substantially unusable for most possible applications takes place within a few hours without the presence of any cations.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the treatment of aqueous fluids by filtration or absorption, characterized in that the filtering or absorbing means is a composition comprising a polyurethane(urea) composition in finely divided or particulate form having water-absorbability of from 33 to 97% by weight and containing
   (i) from 3 to 95% by weight of a synthetic resin foam in the form of particles,
   (ii) from 0 to 90% by weight of lignite and/or peat, and
   (iii) from 0 to 90% by weight of other organic and/or inorganic fillers wherein the total amount of components (i), (ii), and (iii) is from 5 to 95% by weight and wherein said percents by weight are based on the total moisture-free weight of said composition.

2. A process for bioconversion of organic materials for the production of organic compounds by use of bacteria or enzymes characterized in that the carrier for the bacteria or enzymes is a composition comprising a polyurethane(urea) composition in finely divided or particulate form having water-absorbability of from 33 to 97% by weight and containing
   (i) from 3 to 95% by weight of a synthetic resin foam in the form of particles,
   (ii) from 0 to 90% by weight of lignite and/or peat, and
   (iii) from 0 to 90% by weight of other organic and/or inorganic fillers wherein the total amount of components (i), (ii) and (iii) is from 5 to 95% by weight and wherein said percents by weight are based on the total moisture-free weight of said composition.

* * * * *